United States Patent [19]

Melief et al.

[11] Patent Number: 5,679,641

[45] Date of Patent: Oct. 21, 1997

[54] PEPTIDES OF HUMAN P53 PROTEIN FOR USE IN HUMAN T CELL RESPONSE INDUCING COMPOSITIONS, AND HUMAN P53 PROTEIN-SPECIFIC CYTOTOXIC T-LYMPHOCYTES

[75] Inventors: Cornelis Joseph Maria Melief, Heemstede; Wybe Martin Kast, Leiden, both of Netherlands

[73] Assignees: Rijksuniversiteit Leiden, Leiden; Seed Capital Investments, (SCI) B.V., Utrecht, both of Netherlands

[21] Appl. No.: 338,634

[22] PCT Filed: May 18, 1993

[86] PCT No.: PCT/NL93/00102

§ 371 Date: Feb. 6, 1995

§ 102(e) Date: Feb. 6, 1995

[87] PCT Pub. No.: WO93/24525

PCT Pub. Date: Dec. 9, 1993

[30] Foreign Application Priority Data

May 26, 1992 [EP] European Pat. Off. .............. 92201510

[51] Int. Cl.$^6$ .............. A61K 38/00; C07K 5/00; C12N 5/00

[52] U.S. Cl. .............. 514/15; 530/327; 530/328; 435/325; 435/372.3

[58] Field of Search ............... 530/300, 327, 530/328; 514/27, 15; 435/325, 327.3

[56] References Cited

FOREIGN PATENT DOCUMENTS 475 623 A1  3/1992  European Pat. Off. ........ A61K 48/00

OTHER PUBLICATIONS

Ezzell, J. NIH Research, 7:46–49, 1995 Jan. 1995.
Ikeda et al., Int. J. Oncology, 8: 1045–1052, 1996 Feb. 1996.
Lotze, Cell transplantation, 2: 33–47, 1993 Feb. 1993.
Melief, et al., Res. Immunol., 142: 425–429, 1991 Jun. 1991.
Leder et al., Peptides 1992, Proc. Eur. Pept. Symp. 22nd., pp. 136–138 Sep. 1992.

Primary Examiner—Christina Y. Chan
Assistant Examiner—Patrick Nolan
Attorney, Agent, or Firm—Hoffmann & Baron, LLP

[57] ABSTRACT

A peptide comprising an amino acid sequence derived from human p53 protein, wherein said amino acid sequence has the ability to bind to a human MHC Class I molecule. Its use in prophylactic or therapeutic treatment of diseases such as human cancers showing p53 protein overexpression, and its use in induction of primary p53-specific T cells that can be used in therapeutic treatment. Its use in diagnostic tests or assays.

7 Claims, No Drawings

SEQUENCE LISTING ( 1 ) GENERAL INFORMATION:

( i i i ) NUMBER OF SEQUENCES: 39

( 2 ) INFORMATION FOR SEQ ID NO: 1:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 1:

```
Asp  Leu  Trp  Lys  Leu  Leu  Pro  Glu  Asn  Asn  Val
 1                  5                           10
```

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 2:

```
Lys  Leu  Leu  Pro  Glu  Asn  Asn  Val  Leu
 1                  5
```

( 2 ) INFORMATION FOR SEQ ID NO: 3:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 3:

```
Leu  Leu  Pro  Glu  Asn  Asn  Val  Leu  Ser
 1                  5
```

( 2 ) INFORMATION FOR SEQ ID NO: 4:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 4:

```
Leu Leu Pro Glu Asn Asn Val Leu Ser Pro Leu
1               5                   10
```

( 2 ) INFORMATION FOR SEQ ID NO: 5:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 5:

```
Arg Met Pro Glu Ala Ala Pro Pro Val
1               5
```

( 2 ) INFORMATION FOR SEQ ID NO: 6:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 6:

```
Arg Met Pro Glu Ala Ala Pro Pro Val Ala
1               5                   10
```

( 2 ) INFORMATION FOR SEQ ID NO: 7:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 7:

```
Glu Ala Ala Pro Pro Val Ala Pro Ala
1               5
```

( 2 ) INFORMATION FOR SEQ ID NO: 8:

( i ) SEQUENCE CHARACTERISTICS:
        ( A ) LENGTH: 11 amino acids
        ( B ) TYPE: amino acid
        ( C ) STRANDEDNESS: unknown (D) TOPOLOGY: unknown (ii) MOLECULE TYPE: peptide (iii) HYPOTHETICAL: NO (xi) SEQUENCE DESCRIPTION: SEQ ID NO: 8:

```
Glu Ala Ala Pro Pro Val Ala Pro Ala Pro Ala
1               5                   10
```

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 9:

```
Phe Leu His Ser Gly Thr Ala Lys Ser Val
1               5                   10
```

(2) INFORMATION FOR SEQ ID NO: 10:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 10:

```
Ala Leu Asn Lys Met Phe Cys Gln Leu
1               5
```

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 11:

```
Ala Leu Asn Lys Met Phe Cys Gln Leu Ala
1               5                   10
```

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 12:

```
    Lys Met Phe Cys Gln Leu Ala Lys Thr
    1               5
```

( 2 ) INFORMATION FOR SEQ ID NO: 13:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 13:

```
    Gln Leu Ala Lys Thr Cys Pro Val Gln Leu
    1               5                   10
```

( 2 ) INFORMATION FOR SEQ ID NO: 14:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 14:

```
    Lys Gln Ser Gln His Met Thr Glu Val
    1               5
```

( 2 ) INFORMATION FOR SEQ ID NO: 15:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 15:

```
    His Met Thr Glu Val Val Arg Arg Cys
    1               5
```

( 2 ) INFORMATION FOR SEQ ID NO: 16:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 16:

```
    Gly Leu Ala Pro Pro Gln His Leu Ile
    1               5
```

( 2 ) INFORMATION FOR SEQ ID NO: 17:

( i ) SEQUENCE CHARACTERISTICS:
        ( A ) LENGTH: 11 amino acids (B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 17:

Gly Leu Ala Pro Pro Gln His Leu Ile Arg Val
1               5                   10

(2) INFORMATION FOR SEQ ID NO: 18:

(i) SEQUENCE CHARACTERISTICS:
    (A) LENGTH: 11 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO: 18:

His Leu Ile Arg Val Glu Gly Asn Leu Arg Val
1               5                   10

(2) INFORMATION FOR SEQ ID NO: 19:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO: 19:

Asp Arg Asn Thr Phe Arg His Ser Val Val
1               5                   10

(2) INFORMATION FOR SEQ ID NO: 20:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO: 20:

Thr Leu Glu Asp Ser Ser Gly Asn Leu Leu
1               5                   10

(2) INFORMATION FOR SEQ ID NO: 21:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (iii) HYPOTHETICAL: NO ( x i ) SEQUENCE DESCRIPTION: SEQ ID NO: 21:

```
Asn Leu Leu Gly Arg Asn Ser Phe Glu Val
1               5                   10
```

( 2 ) INFORMATION FOR SEQ ID NO: 22:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 22:

```
Leu Leu Gly Arg Asn Ser Phe Glu Val
1               5
```

( 2 ) INFORMATION FOR SEQ ID NO: 23:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 23:

```
Leu Leu Gly Arg Asn Ser Phe Glu Val Arg Val
1               5                   10
```

( 2 ) INFORMATION FOR SEQ ID NO: 24:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 24:

```
Leu Pro Pro Gly Ser Thr Lys Arg Ala
1               5
```

( 2 ) INFORMATION FOR SEQ ID NO: 25:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO: 25:

```
Glu Met Phe Arg Glu Leu Asn Glu Ala
1               5
```

( 2 ) INFORMATION FOR SEQ ID NO: 26:

( i ) SEQUENCE CHARACTERISTICS:
  ( A ) LENGTH: 9 amino acids
  ( B ) TYPE: amino acid
  ( C ) STRANDEDNESS: unknown
  ( D ) TOPOLOGY: unknown ( i i ) MOLECULE TYPE: peptide ( i i i ) HYPOTHETICAL: NO ( x i ) SEQUENCE DESCRIPTION: SEQ ID NO: 26:

Ala Leu Asn Lys Met Leu Cys Gln Leu
1               5

( 2 ) INFORMATION FOR SEQ ID NO: 27:

( i ) SEQUENCE CHARACTERISTICS:
    ( A ) LENGTH: 10 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 27:

Ala Leu Asn Lys Met Phe Tyr Leu Gln Leu
1               5                   10

( 2 ) INFORMATION FOR SEQ ID NO: 28:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 28:

Asn Met Phe Cys Gln Leu Ala Lys Thr
1               5

( 2 ) INFORMATION FOR SEQ ID NO: 29:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 29:

Lys Leu Phe Cys Gln Leu Ala Lys Thr
1               5

( 2 ) INFORMATION FOR SEQ ID NO: 30:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 30:

Lys Met Phe Tyr Gln Leu Ala Lys Thr
1               5

( 2 ) INFORMATION FOR SEQ ID NO: 31:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 31:

Lys Thr Tyr Pro Val Gln Leu Trp Val
1               5

( 2 ) INFORMATION FOR SEQ ID NO: 32:

( i ) SEQUENCE CHARACTERISTICS:
    ( A ) LENGTH: 10 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 32:

Lys Gln Ser Gln His Met Thr Glu Val Leu
1               5                   10

( 2 ) INFORMATION FOR SEQ ID NO: 33:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 33:

His Met Thr Glu Val Val Arg His Cys
1               5

( 2 ) INFORMATION FOR SEQ ID NO: 34:

( i ) SEQUENCE CHARACTERISTICS:
    ( A ) LENGTH: 11 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( x i ) SEQUENCE DESCRIPTION: SEQ ID NO: 34:

Gly Leu Ala Pro Pro Gln His Phe Ile Arg Val
1               5                   10

( 2 ) INFORMATION FOR SEQ ID NO: 35:

( i ) SEQUENCE CHARACTERISTICS:
　　　　( A ) LENGTH: 9 amino acids
　　　　( B ) TYPE: amino acid
　　　　( C ) STRANDEDNESS: unknown
　　　　( D ) TOPOLOGY: unknown ( i i ) MOLECULE TYPE: peptide ( i i i ) HYPOTHETICAL: NO ( x i ) SEQUENCE DESCRIPTION: SEQ ID NO: 35:

```
Asn Gln Arg Pro Ile Leu Thr Ile Ile
1               5
```

( 2 ) INFORMATION FOR SEQ ID NO: 36:

( i ) SEQUENCE CHARACTERISTICS:
　　　　( A ) LENGTH: 11 amino acids
　　　　( B ) TYPE: amino acid
　　　　( C ) STRANDEDNESS: unknown
　　　　( D ) TOPOLOGY: unknown ( i i ) MOLECULE TYPE: peptide ( i i i ) HYPOTHETICAL: NO ( x i ) SEQUENCE DESCRIPTION: SEQ ID NO: 36:

```
Thr Leu Glu Asp Ser Ser Gly Asn Leu Leu Val
1               5                   10
```

( 2 ) INFORMATION FOR SEQ ID NO: 37:

( i ) SEQUENCE CHARACTERISTICS:
　　　　( A ) LENGTH: 9 amino acids
　　　　( B ) TYPE: amino acid
　　　　( C ) STRANDEDNESS: unknown
　　　　( D ) TOPOLOGY: unknown ( i i ) MOLECULE TYPE: peptide ( i i i ) HYPOTHETICAL: NO ( x i ) SEQUENCE DESCRIPTION: SEQ ID NO: 37:

```
Leu Leu Val Arg Asn Ser Phe Glu Val
1               5
```

( 2 ) INFORMATION FOR SEQ ID NO: 38:

( i ) SEQUENCE CHARACTERISTICS:
　　　　( A ) LENGTH: 10 amino acids
　　　　( B ) TYPE: amino acid
　　　　( C ) STRANDEDNESS: unknown
　　　　( D ) TOPOLOGY: unknown ( i i ) MOLECULE TYPE: peptide ( i i i ) HYPOTHETICAL: NO ( x i ) SEQUENCE DESCRIPTION: SEQ ID NO: 38:

```
Leu Leu Gly Arg Asn Ser Phe Glu Val Cys
1               5                   10
```

( 2 ) INFORMATION FOR SEQ ID NO: 39:

( i ) SEQUENCE CHARACTERISTICS:
　　　　( A ) LENGTH: 11 amino acids
　　　　( B ) TYPE: amino acid
　　　　( C ) STRANDEDNESS: unknown
　　　　( D ) TOPOLOGY: unknown ( i i ) MOLECULE TYPE: peptide ( i i i ) HYPOTHETICAL: NO ( x i ) SEQUENCE DESCRIPTION: SEQ ID NO: 39:

```
Leu Leu Gly Arg Asn Ser Phe Glu Val Cys Val
1               5                   10
```

PEPTIDES OF HUMAN P53 PROTEIN FOR USE IN HUMAN T CELL RESPONSE INDUCING COMPOSITIONS, AND HUMAN P53 PROTEIN-SPECIFIC CYTOTOXIC T-LYMPHOCYTES

The present application is a 371 of PCT/NL 03/00102, filed May 18, 1993.

FIELD OF THE INVENTION

The invention is concerned with novel peptides derived from the human p53 protein. The invention further concerns the use of said novel peptides in: (1) the induction of primary p53-specific T cells that can be used in a therapeutic treatment, in particular the induction of HLA class I-restricted CD8$^+$ cytotoxic T cells and (2) pharmaceutical compositions for a prophylactic or therapeutic treatment of human individuals, all against diseases such as a variety of human cancers that show an overexpressed p53 protein.

BACKGROUND OF THE INVENTION

Human protein p53 is a nuclear phosphoprotein that is involved in regulation of the cell cycle. It is expressed by many normal cells (1). Although p53 has been implicated as a proto-oncogene, the molecular mechanisms of p53 action in normal and malignant cells are not well understood. It has been demonstrated, however, that the p53 gene frequently acquires mutations during the development of many human malignancies including colon, breast, lung, leukemias, soft tissue sarcomas, bladder, ovary, brain and neurofibrosarcomas in patients with von Recklinghausen disease (2-9). The p53 mutations which have been noted in these cancers invariably are located in a relatively large region of the gene that has been highly conserved through evolution (10). These mutations, which cause amino acid substitutions, appear to change the conformation of p53 resulting in increased stability and higher steady state levels of this normally short lived protein (11). It is precisely this difference between normal cells and tumor cells that our invention is concerned with, because it would allow the induction of T cell immune responses against this overexpressed p53 protein. Such T cells would subsequently only react against tumor cells with overexpression of p53 protein and not against normal cells with minimal expression of p53. These T cells would not necessarily have to react against the mutated amino acid sequences of p53 (although they could), but this invention is especially concerned with the reaction of T cells against normal amino acid sequences of p53 to which one would expect immunological tolerance. These normal autologous p53 antigens can also be overexpressed in tumors because of mutations elsewhere in the p53 protein sequence.

Cytotoxic T lymphocytes (CTL) are of crucial importance in the resistance against virus infections and the immune surveillance against tumors (reviewed in 12 and 13). CTL specific for viruses or tumors recognize short viral or tumor protein-derived peptides, of about 9 amino acids in length, that are bound to the antigen presenting groove of major histocompatibility complex (MHC) class I molecules (reviewed in 12 and 13). Recently in several systems vaccination with peptides recognized by antigen-specific CTL was shown to prevent lethal virus infections and to delay tumor growth in mice (reviewed in 12 and 14).

We have succeeded in the identification of autologous human p53 peptides that bind to the groove of MHC class I molecules by using the antigen processing defective cell line 174.CEM T2 generated and provided by P. Cresswell (15). This cell line expresses the human MHC class I HLA-A2.1 and HLA-B5 alleles of which only the HLA-A2.1 molecules are expressed as partly empty and unstable molecules that can be stabilized on the cell surface with exogenously added peptides. Addition of human β2-microglobulin enhances peptide-loaded MHC class I expression on 174.CEM T2 cells. Subsequent primary CTL response induction (see further on) can also be enhanced. If incubation with peptide results in an increase in the cell surface expression of this MHC molecule, this implies that the peptide binds to the groove of the HLA-A2.1 molecule and is therefore a possible candidate to be recognized by CTL. The HLA-A2.1 molecule is the most frequent HLA molecule present in the Western European Caucasoid population. About 50% of this population expresses this allele.

We developed a computer scoring system for predicting binding of peptides to HLA-A2.1 that is based on a 9 amino acid long peptide "motif" rule suggested in the literature (17). This peptide motif was edited on basis of recent literature (27), similarities in chemical properties among some amino acids and testing of the binding capacity to HLA-A2.1 of hundreds of peptides in our laboratory. This editing resulted in designation to the HLA-A2.1 specific motif of additional "anchor" residues: i.e. isoleucine and methionine at position 2 and leucine, isoleucine, alanine, cysteine and threonine at the C-terminal end.

Based on experience in our laboratory the scoring system was developed as follows: so called "anchor" residues in a peptide are assigned 6 points, "strong" residues 4 points and "weak" residues 2 points. The scores of all 9 amino acids are multiplied to reach the final peptide score. Peptide binding experiments in our laboratory showed that 10 or 11 amino acid long peptides (synonym: 10-met or 11-mer peptides) can bind to HLA-A2.1. The scoring for 10-mer and 11-mer peptides is performed comparibly to 9-mer peptides, but multiple anchors at positions 9, 10 or 11 within one peptide are scored only once. Furthermore, 10-mer and 11-mer peptides lacking anchor residues at the C-terminal end are discarded. The minimum score of a 9-mer, 10-mer or 11-mer peptide to be synthesized and tested was 72 points.

The significance of the edited peptide motif was demonstrated in our laboratory when all overlapping 9-mer peptides of the E6 and E7 protein of Human Papilloma Virus were tested on binding to HLA-A2.1. The number of scoring points correlated with the chance for binding to HLA-A2.1.

Scoring of the whole human (mutant) p53 protein using the edited peptide motif and the above mentioned scoring system resulted in 104 wild-type peptides out of the 1152 possible wild-type p53 peptides scoring more than 71 scoring points and 36 mutant peptides out of the 1020 possible peptides of 34 different mutations of p53 described for colon, ovarian and lung cancer scoring more than 71 scoring points. The 43 plus 19 9-mer, 34 plus 8 10-met and 27 plus 9 11-mer peptides were synthesized. Each of the 140 peptides was individually tested with respect to its capacity to bind to the HLA-A2.1 molecule. In total 25 peptides of the natural human p53 protein and 14 peptides of mutant p53 were identified to bind to the HLA-A2.1 molecule.

Furthermore, we have been able to mount a primary in vitro human CTL response against some of these peptides by using the peptide loaded antigen processing defective cell line 174.CEM T2. This method is the subject of a co-pending patent application by us. It must be stressed that the reaction of these CTL against autologous non-mutated human p53 peptides is highly unexpected. This implies that the important candidate peptides of the natural and non-mutated human p53 protein for use as a vaccine in HLA-A2.1 positive humans have been identified and also the peptides of natural p53 that can be used to stimulate human p53 specific CTL responses in vitro. Such CTL could subsequently be used for adoptive transfer into patients for treatment of cancers that overexpress p53 proteins.

A purpose of the present invention is therefore to provide specific synthetic peptides of the natural or mutated p53 protein for prevention, prophylaxis, therapy and treatment of diseases in human beings such as a variety of human cancers that show an overexpressed p53 protein utilizing these synthetic peptides and pharmaceutical compositions containing the synthetic peptides. A further purpose of the present invention is to provide CTL which are reactive against natural or mutated human p53 protein and are useful for prevention, prophylaxis, therapy and treatment of the above mentioned diseases in human beings.

SUMMARY OF THE INVENTION

The present invention provides specific peptides derived from the amino acid sequence of the human p53 protein which, because of their capability to bind to the HLA-2.1 protein, are candidate peptides to be included in human vaccines that can induce protective or therapeutic T cell responses against human cancers in which p53 is overexpressed.

The novel peptides of the present invention are useful in pharmaceutical compositions, as screening tools and in the prevention, prophylaxis, therapy and treatment of diseases or other conditions which would benefit from inhibition of p53 overexpression.

This invention provides a peptide comprising an amino acid sequence derived from human p53 protein, wherein said: amino acid sequence has the ability to bind to a human MHC Class I molecule.

Preferably, said amino acid sequence has the ability to bind to human MHC Class I allele HLA-A2.1.

More specifically, this invention provides a peptide comprising an amino acid sequence derived from human (wild-type or mutant) p53 protein, wherein said amino acid sequence has the ability to bind to human MHC Class I allele HLA-A2.1 and is selected from the group consisting of:

| 1.  | DLWKLLPENNV  | (residues 21–31 of human p53)  | SEQ ID NO:1 |
| --- | --- | --- | --- |
| 2.  | KLLPENNVL    | (residues 24–32 of human p53)  | SEQ ID NO:2 |
| 3.  | LLPENNVLS    | (residues 25–33 of human p53)  | SEQ ID NO:3 |
| 4.  | LLPENNVLSPL  | (residues 25–35 of human p53)  | SEQ ID NO:4 |
| 5.  | RMPEAAPPV    | (residues 65–73 of human p53)  | SEQ ID NO:5 |
| 6.  | RMPEAAPPVA   | (residues 65–74 of human p53)  | SEQ ID NO:6 |
| 7.  | EAAPPVAPA    | (residues 68–76 of human p53)  | SEQ ID NO:7 |
| 8.  | EAAPPVAPAPA  | (residues 68–78 of human p53)  | SEQ ID NO:8 |
| 9.  | FLHSGTAKSV   | (residues 113–122 of human p53) | SEQ ID NO:9 |
| 10. | ALNKMFCQL    | (residues 129–137 of human p53) | SEQ ID NO:10 |
| 11. | ALNKMFCOLA   | (residues 129–138 of human p53) | SEQ ID NO:11 |
| 12. | KMFCQLAKT    | (residues 132–140 of human p53) | SEQ ID NO:12 |

-continued

| 13. | QLAKTCPVQL   | (residues 136–145 of human p53) | SEQ ID NO:13 |
| --- | --- | --- | --- |
| 14. | KQSQHMTEV    | (residues 164–172 of human p53) | SEQ ID NO:14 |
| 15. | HMTEVVRRC    | (residues 168–176 of human p53) | SEQ ID NO:15 |
| 16. | GLAPPQHLI    | (residues 187–195 of human p53) | SEQ ID NO:16 |
| 17. | GLAPPQHLIRV  | (residues 187–193 of human p53) | SEQ ID NO:17 |
| 18. | HLIRVEGNLRV  | (residues 193–203 of human p53) | SEQ ID NO:18 |
| 19. | DRNTFRHSVV   | (residues 208–217 of human p53) | SEQ ID NO:19 |
| 20. | TLEDSSGNLL   | (residues 256–265 of human p53) | SEQ ID NO:20 |
| 21. | NLLGRNSFEV   | (residues 263–272 of human p53) | SEQ ID NO:21 |
| 22. | LLGRNSFEV    | (residues 264–272 of human p53) | SEQ ID NO:22 |
| 23. | LLGRNSFEVRV  | (residues 264–274 of human p53) | SEQ ID NO:23 |
| 24. | LPPGSTKRA    | (residues 299–307 of human p53) | SEQ ID NO:24 |
| 25. | EMFRELNEA    | (residues 339–347 of human p53) | SEQ ID NO:25 |
| 26. | ALNKMLCQL    | (residues 129–137 of human mp53) | SEQ ID NO:26 |
| 27. | ALNKMFYQL    | (residues 129–137 of human mp53) | SEQ ID NO:27 |
| 28. | NMFCQLAKT    | (residues 132–140 of human mp53) | SEQ ID NO:28 |
| 29. | KLFCQLAXT    | (residues 132–140 of human mp53) | SEQ ID NO:29 |
| 30. | KMFYQLAKT    | (residues 132–140 of human mp53) | SEQ ID NO:30 |
| 31. | KTYPVQLWV    | (residues 139–147 of human mp53) | SEQ ID NO:31 |
| 32. | KQSQHMTEVL   | (residues 164–173 of human mp53) | SEQ ID NO:32 |
| 33. | HMTEVVRHC    | (residues 168–176 of human mp53) | SEQ ID NO:33 |
| 34. | GLAPPQHFIRV  | (residues 187–197 of human mp53) | SEQ ID NO:34 |
| 35. | NQRPILTII    | (residues 247–255 of human mp53) | SEQ ID NO:35 |
| 36. | TLEDSSGNLLV  | (residues 256–266 of human mp53) | SEQ ID NO:36 |
| 37. | LLVRNSFEV    | (residues 264–272 of human mp53) | SEQ ID NO:37 |
| 38. | LLGRNSFEVC   | (residues 264–273 of human mp53) | SEQ ID NO:38 |
| 39. | LLGRNSFEVCV  | (residues 264–274 of human mp53) | SEQ ID NO:39 |

40. a fragment, homolog, isoform, derivative, genetic variant or conservative variant of any one of the amino acid sequences Nos. 1–39 which has the ability to bind.to human MHC Class I allele HLA-A2.1.

This invention further provides a pharmaceutical composition containing a prophylactically or therapeutically effective amount of a peptide according to the invention, and a pharmaceutically acceptable carrier, diluent, excipient or adjuvant. Preferably, said pharmaceutical composition contains a peptide according to the invention which is able to induce a T cell response effective against human p53 protein, more particularly a HLA class I-restricted CD8$^+$ cytotoxic T cell response effective against human p53-protein.

In addition, this invention provides a method of prophylactic or therapeutic treatment of diseases such as a variety of human cancers that show an overexpressed p53 protein, with a human individual, comprising administering to said human individual a prophylactically or therapeutically effective amount of a peptide according to the invention, more specifically an immunogenic form of a peptide according to the invention which is able to induce a T cell response effective against human p53 protein, more particularly a HLA class I-restricted CD8⁺ cytotoxic T cell response effective against human p53 protein.

Furthermore, it has been possible so far to generate a primary in vitro human CTL response against the peptides Nos. 3, 5, 9 and 22 of the natural human p53 protein sequence by using the peptide loaded antigen processing defective cell line 174.CEM T2. The other peptides remain to be tested but are certainly good candidate peptides to induce comparable CTL responses. These human p53-specific CTL can be used for adoptive transfer into patients for treatment of diseases such as a variety of human cancers in which p53 protein is overexpressed.

Consequently, the invention further provides a process of inducing a human p53 protein-specific CTL response in a T-lymphocyte culture, comprising the steps of loading antigen-presenting cells which carry empty MHC Class I molecules with a peptide according to the invention, culturing T-lymphocytes in the presence of the peptide-loaded antigen-presenting cells under specific CTL response-inducing conditions, and, optionally, isolating a human p53 protein-specific CTL from the resulting culture and culturing said isolated CTL.

The invention covers a human p53 protein-specific CTL reactive to a peptide according to the invention, a pharmaceutical composition containing a prophylactically or therapeutically effective amount of a human p53 protein-specific specific CTL reactive to a peptide according to the invention and a pharmaceutically acceptable carrier, diluent, excipient or adjuvant, and a method of prophylactic or therapeutic treatment of diseases showing p53 protein overexpression with a human individual, comprising administering to said human individual a prophylactically or therapeutically effective amount of a human p53 protein-specific CTL reactive to a peptide according to the invention.

The invention provides a peptide as defined herein for prophylactically or therapeutically inducing in a human individual a HLA class I-restricted CD8⁺ cytotoxic T cell response effective against human p53 protein.

The invention covers the use of a peptide as defined herein for preparing a pharmaceutical composition for prophylactically or therapeutically inducing in a human individual a HLA class I-restricted CD8⁺ cytotoxic T cell response effective against human p53 protein.

The invention also covers the use of a peptide as defined herein in a diagnostic test or assay to detect human p53 protein-specific T cells or antibodies.

DETAILED DESCRIPTION OF THE INVENTION

The invention is directed to peptides comprising an amino acid sequence derived from human p53 protein, wherein said amino acid sequence has the ability to bind to a human MHC Class I molecule. A most preferred embodiment of the invention concerns peptides comprising an amino acid sequence derived from human p53 protein, wherein said amino acid sequence has the ability to bind to human MHC Class I allele HLA-A2.1. Specifically, such peptides comprise the following amino acid sequences derived from human (wild-type or mutant) p53 protein (see Table 1; the amino acids are identified by the one-letter code of amino acids; mp53 stands for mutant p53; the underlined letter is the mutation).

TABLE 1

| No. | Amino acid sequence | location in human p53 protein | SEQ ID NO |
|---|---|---|---|
| 1. | DLWKLLPENNV | (residues 21–31 of human p53) | SEQ ID NO:1 |
| 2. | KLLPENNVL | (residues 24–32 of human p53) | SEQ ID NO:2 |
| 3. | LLPENNVLS | (residues 25–33 of human p53) | SEQ ID NO:3 |
| 4. | LLPENNVLSPL | (residues 25–35 of human p53) | SEQ ID NO:4 |
| 5. | RMPEAAPPV | (residues 65–73 of human p53) | SEQ ID NO:5 |
| 6. | RMPEAAPPVA | (residues 65–74 of human p53) | SEQ ID NO:6 |
| 7. | EAAPPVAPA | (residues 68–76 of human p53) | SEQ ID NO:7 |
| 8. | EAAPPVAPAPA | (residues 68–78 of human p53) | SEQ ID NO:8 |
| 9. | FLHSGTAKSV | (residues 113–122 of human p53) | SEQ ID NO:9 |
| 10. | ALNKMFCQL | (residues 129–137 of human p53) | SEQ ID NO:10 |
| 11. | ALNKMFCQLA | (residues 129–138 of human p53) | SEQ ID NO:11 |
| 12. | KMFCQLAKT | (residues 132–140 of human p53) | SEQ ID NO:12 |
| 13. | QLAKTCPVQL | (residues 136–145 of human p53) | SEQ ID NO:13 |
| 14. | KQSQHMTEV | (residues 164–172 of human p53) | SEQ ID NO:14 |
| 15. | HMTEVVRRC | (residues 168–176 of human p53) | SEQ ID NO:15 |
| 16. | GLAPPQHLI | (residues 187–195 of human p53) | SEQ ID NO:16 |
| 17. | GLAPPQHLIRV | (residues 187–193 of human p53) | SEQ ID NO:17 |
| 18. | HLIRVEGNLRV | (residues 193–203 of human p53) | SEQ ID NO:18 |
| 19. | DRNTFRHSVV | (residues 208–217 of human p53) | SEQ ID NO:19 |
| 20. | TLEDSSGNLL | (residues 256–265 of human p53) | SEQ ID NO:20 |
| 21. | NLLGRNSFEV | (residues 263–272 of human p53) | SEQ ID NO:21 |
| 22. | LLGRNSFEV | (residues 264–272 of human p53) | SEQ ID NO:22 |
| 23. | LLGRNSFEVRV | (residues 264–274 of human p53) | SEQ ID NO:23 |
| 24. | LPPGSTKRA | (residues 299–307 of human p53) | SEQ ID NO:24 |
| 25. | EMFRELNEA | (residues 339–347 of human p53) | SEQ ID NO:25 |
| 26. | ALNKMLCQL | (residues 129–137 of human mp53) | SEQ ID NO:26 |
| 27. | ALNKMFYQL | (residues 129–137 of human mp53) | SEQ ID NO:27 |
| 28. | NMFCQLAKT | (residues 132–140 of human mp53) | SEQ ID NO:28 |
| 29. | KLFCQLAXT | (residues 132–140 of human mp53) | SEQ ID NO:29 |
| 30. | KMFYQLAKT | (residues 132–140 of human mp53) | SEQ ID NO:30 |
| 31. | KTYPVQLWV | (residues 139–147 of human mp53) | SEQ ID NO:31 |
| 32. | KQSQHMTEVL | (residues 164–173 of human mp53) | SEQ ID NO:32 |
| 33. | HMTEVVRHC | (residues 168–176 of human mp53) | SEQ ID NO:33 |
| 34. | GLAPPQHFIRV | (residues 187–197 of human mp53) | SEQ ID NO:34 |
| 35. | NQRPILTII | (residues 247–255 of human mp53) | SEQ ID NO:35 |
| 36. | TLEDSSGNLLV | (residues 256–266 of human mp53) | SEQ ID NO:36 |
| 37. | LLVRNSFEV | (residues 264–272 of human mp53) | SEQ ID NO:37 |
| 38. | LLGRNSFEVC | (residues 264–273 of human mp53) | SEQ ID NO:38 |

TABLE 1-continued

| No. | Amino acid sequence | location in human p53 protein | SEQ ID NO |
|---|---|---|---|
| 39. | LLGRNSFEVCV | (residues 264–274 of human mp53) | SEQ ID NO:39 |

The data suggest that the peptides mentioned above are single polypeptides of identified sequences. However, homologs, isoforms or genetic variants of these peptides may exist within or outside the cellular environment. This invention encompasses all such homologs, isoforms or genetic variants of the above peptides provided that they bind to the HLA molecule in question. Polypeptides that are homologs of the peptides specifically include those having amino acid sequences which are at least about 40% conserved in relation to the amino acid sequence set forth in Table 1, preferentially at least about 60% conserved, and more preferentially at least about 75% conserved.

It will be understood by one of ordinary skill in the art that other variants of the peptides shown above are included within the scope of the present invention. This particularly includes any variants that differ from the above mentioned and synthesized peptides only by conservative amino acid substitution. In particular, replacements of C (cysteine) by A (alanine), S (serine), α-aminobutyric acid and others are included as it is known that cysteine-containing peptides are susceptible to (air) oxidation during synthesis and handling. Many such conservative amino acid substitutions are set forth as sets in ref. 18. Especially included within the scope of the present invention are mutated sequences that may occur in cancer cells. Generally, the mutation concerns one amino acid residue, but plural mutations, especially in two amino acid residues, may also occur.

The 34 mutations of p53 described for colon, ovarian and lung cancer that were used to define potentially binding peptides of mutant p53 are listed below. The result of the mutation, i.e. the amino acid sequence (in one letter code) and the position in p53 is listed below. It must be noted that frequently newly discovered mutations of p53 are published.

| No. | amino acid position | wild-type amino acid | result of mutation |
|---|---|---|---|
| 1 | 132 | K | N |
| 2 | 133 | M | L |
| 3 | 132–133 | KM | NL |
| 4 | 134 | F | L |
| 5 | 135 | C | Y |
| 6 | 135 | C | T |
| 7 | 141 | C | Y |
| 8 | 143 | V | A |
| 9 | 151 | P | S |
| 10 | 154 | G | V |
| 11 | 156 | R | P |
| 12 | 157 | V | F |
| 13 | 159 | A | V |
| 14 | 173 | V | L |
| 15 | 175 | R | H |
| 16 | 176 | C | F |
| 17 | 194 | L | F |
| 18 | 211 | T | A |
| 19 | 216 | V | M |
| 20 | 220 | Y | C |
| 21 | 239 | N | S |
| 22 | 241 | S | F |
| 23 | 247 | N | I |
| 24 | 248 | R | W |

-continued

| No. | amino acid position | wild-type amino acid | result of mutation |
|---|---|---|---|
| 25 | 248 | R | Q |
| 26 | 249 | R | S |
| 27 | 266 | G | V |
| 28 | 272 | V | M |
| 29 | 273 | R | H |
| 30 | 273 | R | C |
| 31 | 273 | R | L |
| 32 | 278 | P | R |
| 33 | 281 | D | G |
| 34 | 282 | R | W |

Peptides according to the invention, or fragments thereof, include any variation in the amino acid sequence, whether by conservative amino acid substitution, deletion, or other process, provided that the polypeptides bind to the HLA molecule in question. The fragments of the peptides may be small peptides with sequences of as little as 5 or more amino acids, said sequences being those disclosed in Table 1 when said polypeptides bind to the HLA-A2.1 molecule.

Polypeptides larger than peptides Nos. 1–39 are especially included within the scope of the present invention when said polypeptides induce a human p53 protein-specific CTL response in appropriate individuals (e.g. HLA-A2.1 positive individuals) and include a (partial) amino acid sequence as set forth in Table 1, or conservative substitutions thereof. Such polypeptides may have a length up to about 30 amino acids, preferably up to about 27 amino acids. Most preferably, however, the peptides have a length of from 9 to 12, more preferably 9 to 11 amino acids.

This invention includes the use of polypeptides Nos. 1–39 generated by every means, whether genetic engineering, peptide synthesis with solid phase techniques or others. The peptides may have various chemical modifications made at the terminal ends and still be within the scope the present invention. Also other chemical modifications are possible, particularly cyclic and dimeric configurations. The term "derivatives" intends to cover all such modified peptides.

The polypeptides of the present invention find utility for the treatment or prevention of diseases involving human p53 protein such as a variety of human cancers.

For all applications the peptides are administered in an immunogenic form. Since the peptides are relatively short, this may necessitate conjugation with an immunogenicity-conferring carrier material such as lipids or others or the use of adjuvants.

The magnitude of a prophylactic or a therapeutic dose of polypeptides of this invention will, of course, vary with the group of patients (age, Sex, weight, etcetera), the nature of the severity of the condition to be treated, the particular polypeptide of this invention and its route of administration. Any suitable route of administration may be employed to achieve an effective dosage of a polypeptide identified by this invention, as well as any dosage form well known in the art of pharmacy. In addition the polypeptides may also be administered by controlled release means and/or delivery devices. They may also be administered in combination with other active substances, such as, in particular, interferons and T-cell activating agents like interleukin-2 etc.

The peptides of this invention may also be useful for other purposes, such as diagnostic use. For example, they may be used to check whether a vaccination with a peptide according to the invention has been successful. This may be done in vitro by testing whether said peptide is able to activate T cells of the vaccinated person. They may be used also in diagnostic tests or assays for the detection of human p53-specific antibodies.

In order to identify human p53 protein peptides that could bind to HLA-A2.1 molecules the amino acid sequence of human p53 protein was examined (16). Nine, ten and eleven amino acid long peptides were chosen because they fit the presently known rules for length of peptides that bind to the groove of HLA-A2.1 molecules (17 and observations in our laboratory).

Only the 39 peptides described in Table 1 were able to significantly upregulate the expression of HLA-A2.1 molecules measured as mean HLA-A2.1 fluorescence of 174.CEM T2 cells indicating their binding to the HLA-A2.1 molecule as described in Example 2.

None of the other human (wild-type or mutant) p53 protein peptides selected on the basis of our computer scoring system for estimating agreement with the edited peptide motif rule were able to do this, despite the fact that they also had an arbitrary score of more than 71 points in our computer scoring system and thus seemed to follow the rules of the described peptide motifs (17). These experiments indicate that only a limited number of peptides (Nos. 1–39) have the ability to bind to the HLA-A2.1 molecule and are therefore the candidates of human p53 protein to be recognized by human CTL because CTL recognize peptides only when bound to HLA molecules. Furthermore, they are the candidates to be used either for vaccination of human beings in prevention or therapy of diseases such as a variety of human cancers with an overexpressed p53 protein or for the in vitro response induction of p53-specific CTL (as described in Example 3) that subsequently can be used for treatment of said diseases.

The following examples illustrate the present invention without limiting the same thereto.

EXAMPLE 1

Materials

Peptide synthesizer: Abimed AMS 422 (Abimed Analysen-Technik GmbH, Langenfeld, Germany).

Synthesis polymer: Tentagel SAC (0.17–0.24 meq/g, Rapp Polymere, Tübingen, Germany).

HPLC equipment: The HPLC system used for analysis and purification of peptides consisted of: autosampler 2157, HPLC pump 2248, variable wavelength monitor VWM 2141, column oven 2155, low pressure mixer, all of Pharmacia Nederland B. V., Woerden, The Netherlands, a Star LC-20 dot matrix printer, Star Micronics Co., Ltd., all parts controlled by a Tandon PCAsl/386sx computer, Tandon Computer Benelux B. V., Amsterdam, The Netherlands.

Lyophylizer: Virtis Centry, The Virtis Company, Inc., Gardiner (NY), USA, equipped with an Alcatel 350C vacuumpump, Alcatel CIT, Malakoff, France, connected to a Christ Alpha RVC vacuo-spin, Martin Christ Gefriertrocknungsanlagen GmbH, Osterode am Harz, Germany.

Centrifuge: MSE Mistral 6L, Beun de Ronde, Abcoude, The Netherlands.

Mass spectrometer: Bioion plasma desorption mass spectrometer (PDMS), Applied Biosystems, Inc., Foster City (Calif.), USA.

Amino acid Analysis: HP Aminoquant, Hewlett Packard, Amstelveen, The Netherlands.

Chemicals: All chemicals were used without further purification unless stated otherwise.

Fmoc (9-fluorenylmethyloxycarbonyl) amino acid were of the L-configuration, bearing the following side chain protecting groups: t-Bu (tert-butyl) for Asp, Glu, Tyr, Ser and Thr; Trt (trityl) for His, Asn and Gln; Pmc (2,2,5,7,8-penta-methylchroman-6-sulfonyl) for Arg; Boc (tert-butyloxy-carbonyl) for Lys, all Novasyn and purchased from Pharmacia Nederland B. V., Woerden, The Netherlands.

Piperidine was purchased from Aldrich Chemie Benelux N. V., Brussels, Belgium.

BOP (benzotriazole-1-yl-oxy-tris-(dimethylamino)-phosphonium hexafluorophosphate) was obtained from Richelieu Biotechnologies, St-Hyacinthe, Canada.

N-methylmorpholin (NMM, Janssen Chimica, Tilburg, The Netherlands) was distilled from NaOH at atmospheric pressure before use.

N-methylpyrrolidone (NMP, Aldrich Chemie) was vacuum-distilled under a nitrogen atmosphere (b.p. 78°–80° C., 18 mm Hg) before use.

Acetonitrile (HPLC-grade) was purchased from Rathburn Chemicals Ltd., Walkerburn, Scotland.

Ether (Baker Analyzed grade), pentane (Baker grade) and acetic acid (Baker Analyzed grade) were purchased from J. T. Baker B. V., Deventer, The Netherlands.

Ethanethiol was obtained from Fluka Chemie, Brussels, Belgium.

Dichloromethane and N,N-dimethylacetamide (DMA) were purchased from Janssen Chimica, Tilburg, The Netherlands.

Trifluoroacetic acid (TFA, z.S. grade) was obtained from Merck-Schuchardt, Hohenbrunn, Germany.

Disposables: Polypropylene reaction vessels containing a PTFE filter were purchased from Abimed Analysen-Technik GmbH, Langenfeld, Germany.

All other disposables used were made of polypropylene and obtained from Sarstedt B. V., Etten-Leur, The Netherlands. Experimental conditions: All experiments were performed at room temperature unless stated otherwise. All Fmoc protected amino acids, synthesis polymers, peptides and TFA were stored at −20° C.

Peptide synthesis

Peptides were synthesized by solid phase strategies on an automated multiple peptide synthesizer (Abimed AMS 422) (19, 20).

The peptides were made in various runs, in each of which 48 different peptides were synthesized simultaneously.

Tentagel SAC (21, 22), a graft polymer of polyethylene glycol spacer arms on a polystyrene matrix, was used as a resin (40–60 mg per peptide, 10 µmol Fmoc amino acid loading).

Repetitive couplings were performed by adding a mixture of 90 µl 10.67 M BOP (23, 24) in NMP, 20 µl NMM in NMP 2/1 (v/v) and 100 µl of an 0.60 M solution of the appropriate Fmoc amino acid (25) in NMP (6-fold excess) to each reaction vessel. At 70% of the reaction time approximately 50 dichloromethane was added to each reaction vessel.

Fmoc-deprotection was performed by adding 3 times 0.8 ml of piperidine/DMA 1/4 (v/v) to each reaction vessel.

Coupling- and deprotection times were increased as the synthesis proceeded, starting with 30 min and 3 times 3 min respectively.

Washings after couplings and Fmoc-deprotections were done with 6 times 1.2 ml DMA. After the required sequence had been reached and the last Fmoc-protection was removed the peptidylresin was washed extensively with DMA, dichloromethane, dichloromethane/ether 1/1 (v/v) and ether respectively, and dried.

Peptide cleavage and isolation

Cleavage of the peptides from the resin and removal of the side chain protecting groups was performed by adding 6 times 200 µl TFA/water 19/1 (v/v) at 5 min intervals to each reaction vessel, thus yielding free carboxylic peptides. For Trp containing peptides TFA/water/ethanethiol 18/1/1 (v/v/v) was used.

Two hours after the first TFA addition the peptides were precipitated from the combined filtrates by addition of 10 ml ether/pentane 1/1 (v/v) and cooling (−20° C. The peptides were isolated by Centrifugation (−20° C., 2500g, 10 min).

After treatment of the pellet with ether/pentane 1/1 (v/v) and isolation by the same centrifugation procedure, the peptides were dried at 45° C. for 15 min.

Each of the peptides was dissolved in 2 ml water (or 2 ml 10 vol. % acetic acid), the solution frozen in liquid nitrogen for 3 min, and lyophylized while being centrifuged (1300 rpm, 8–16 h).

Analysis and purification

The purity of the peptides was determined by reversed phase HPLC; an aliquot of about 50 nmol was dissolved in 100 µl 30 vol. % acetic acid. Of this solution 30 µl was applied to an RP-HPLC system equipped with a ternary solvent system; A: water, B: acetonitrile, C: 2 vol. % TFA in water.

Gradient elution (1.0 ml/min) was performed from 90% A, 5% B, 5% C to 20% A, 75% B, 5%C in 30 min. Detection was at 214 nm.

Samples taken at random were analysed by mass spectrometry on a PDMS. The 8 binding peptides were all analysed by mass spectrometry on a PDMS and by quantative amino acid analysis after hydrolysis on a HP Aminoquant. Of all analysed samples the difference between calculated and measured masses was within the experimental error (0.1%) as specified by the producer of the equipment used. All aminoacid compositions were as expected.

EXAMPLE 2

From all 140 peptides that had been freeze dried, 5 mg was weighed and dissolved in 1 ml of distilled water. Peptides that did not readily dissolve were treated with 150 µl of 100% acetic acid glacial ($CH_3COOH$, Merck Darmstadt, Germany: 56–1000) after which the pH was neutralized to pH7 with 5N NaOH diluted in distilled water (Merck Darmstadt, Germany: 6498). Of all peptides a dilution of 1 mg/ml in 0.9% NaCl was made.

Cells (174.CEM) T2 cells were cultured in Iscove's modified DULBECCO's medium (Biochrom KG Seromed Berlin, Germany: F0465) supplemented with 100IU/ml penicillin (Biocades Pharma, Leiderdorp, The Netherlands), 100 µg/ml kanamycin (Sigma St. Louis, USA:K-0254), 2 mM glutamine (ICN Biomedicals Inc. Costa Mesa, Calif., USA:15-801-55) and 10% fetal calf serum (FCS, Hyclone Laboratories Inc. Logan, Utah, USA:A-1115-L). Cells were cultured at a density of $2.5 \times 10^5$/ml during 3 days at 37° C., 5% $CO_2$ in humified air.

Peptide binding (174.CEM) T2 cells were washed twice in culture medium without FCS and put, at a density of $2 \times 10^6$ cells/ml in serum free culture medium. Of this suspension 40 µl was put into a V bottommed 96 well plate (Greiner GmbH, Frickenhausen, Germany: 651101) together with 10 µl of the individual peptide dilutions (of 1 mg/ml). The end concentration is 200 µg/ml peptide with $8 \times 10^4$ (174.CEM) T2 cells. This solution was gently agitated for 3 minutes after which an incubation time of 16 hours at 37° C., 5% $CO_2$ in humified air took place. Then cells were washed once with 100 µl 10.9% NaCl, 0.5% bovine serum albumin (Sigma St. Louis, USA:A-7409), 0.02% $NaN_3$ (Merck Darmstadt, Germany:822335). After a centrifuge round of 1200 rpm the pellet was resuspended in 50 µl of saturating amounts of HLA-A2.1 specific mouse monoclonal antibody BB7.2 for 30 minutes at 4° C. Then cells were washed twice and incubated for 30 minutes with F(ab)2 fragments of goat anti-mouse IgG that had been conjugated with fluorescein isothiocyanate (Tago Inc Burlingame, Calif., USA: 4350) in a dilution of 1:40 and a total volume of 25 µl.

After the last incubation, cells were washed twice and fluorescence was measured at 488 nanometer on a FACScan flowcytometer (Becton Dickinson, Franklin Lakes, N.J., USA).

The (174.CEM) T2 cell line expresses "empty" and unstable HLA-A2.1 molecules that can be stabilized when a peptide is binding to the peptide presenting groove of these molecules. A stabilized HLA-A2.1 molecule that will not easily degrade is the result of binding of an analyzed peptide. This leads to an increase in cell surface expression of the HLA-A2.1 molecule. Part of the result of the binding analyses of the 104 wild-type p53 peptides and the 36 mutant p53 peptides is given in Table 2. The 39 binding peptides are all shown and are numbered 1 to 39, while some examples of high scoring but non-binding peptides are numbered A to K.

Binding of peptides is shown as the mean fluorescence level of HLA-A2.1 expression in the presence of said peptides divided by the mean fluorescence level of HLA-A2.1 expression without the presence of said peptides, i.e. the fluorescence ratio. Binding of a peptide is regarded as positive when a fluorescence ratio of 1.2 is reached.

TABLE 2

| human (mutant) p53 peptides | fluorescence ratio (i.e. binding ability) |
|---|---|
| 1 | 1.2 |
| 2 | 1.7 |
| 3 | 1.7 |
| 4 | 2.8 |
| 5 | 2.2 |
| 6 | 1.4 |
| 7 | 1.4 |
| 8 | 1.3 |
| 9 | 1.3 |
| 10 | 1.3 |
| 11 | 1.4 |
| 12 | 1.2 |
| 13 | 1.3 |
| 14 | 1.2 |
| 15 | 1.2 |
| 16 | 1.2 |
| 17 | 2.6 |
| 18 | 1.4 |
| 19 | 1.2 |
| 20 | 1.3 |
| 21 | 1.6 |
| 22 | 1.9 |
| 23 | 1.2 |
| 24 | 1.2 |
| 25 | 1.8 |
| 26 | 1.4 |
| 27 | 1.2 |
| 28 | 1.5 |
| 29 | 1.3 |
| 30 | 1.3 |
| 31 | 1.2 |
| 32 | 1.3 |
| 33 | 1.3 |
| 34 | 1.2 |

TABLE 2-continued

| human (mutant) p53 peptides | fluorescence ratio (i.e. binding ability) |
|---|---|
| 35 | 1.2 |
| 36 | 1.8 |
| 37 | 1.6 |
| 38 | 1.2 |
| 39 | 1.2 |
| A | 1.0 |
| B | 1.0 |
| C | 1.0 |
| D | 1.0 |
| E | 1.0 |
| F | 1.0 |
| G | 1.0 |
| H | 1.0 |
| I | 1.0 |
| J | 1.1 |
| K | 1.1 |

EXAMPLE 3

Primary CTL response induction against autologous p53 tumor suppressor peptide loaded into empty HLA-A2.1 MHC class I molecules at the surface of 174CEM.T2 processing defective cells.

Methods

1. Blood donors

Blood donors were normal healthy blood donors expressing the HLA-A2.1 allele Upon routine NIM microcytotoxicity HLA typing.

2. Responder cells

Responder T cells are included in mononuclear white blood cells (PBL) of an HLA-A2.1 positive healthy donor. The PBL were separated from a buffycoat by Ficoll procedure (LYMPHOPREP of Nycomed-pharma, Oslo, Norway, cat. no. 105033) and washed two times in RPMI 1640 (Gibco Paislan, Scotland, cat. no. 041-02409) supplemented with 30% pooled human serum (tested for its capacity to support mixed lymphocyte cultures), 2 mM glutamine (ICN Biochemicals, Inc., Costa Mesa, Calif., USA, cat. no. 15-801-55), penicillin (100 IU/ml, Brocades Pharma, Leiderdorp, The Netherlands), kanamycin (100 Bg/ml, Sigma, St. Louis, Mo., USA).

3. p53 Peptides

Four p53 peptides from the normal nonmutated p53 sequence (peptides 3, 5, 9 and 22) with strong ability to bind to HLA-A2.1 by the assay described under Example 2 were used for primary CTL response induction by peptide presentation on processing defective 174CEM.T2 cells. These peptides had a free carboxy terminus and were synthesized on a Biosearch (Millipore, Bedford, Mass., USA) 9500 peptide synthesizer according to Merrifield (26), dissolved in PBS or serum-free ISCOVE's modified DULBECCO's medium (IMDM, Flow Laboratories, Irvine, Scotland) and stored at −20° C.

4. Induction of primary CTL response

174CEM.T2 (T2) cells in a concentration of $2\times10^6$ per ml were incubated for 13 hours at 37° C. in a T25 flask (Falcon, Becton & Dickinson, Plymouth, England, cat. no. 3013) in serum-free ISCOVE's medium (Biochrom KG, Seromed, Berlin, Gemany, cat. no. F0465) with glutamine (2 mM, ICN Biochemicals Inc., Costa Mesa, Calif., USA, cat. no. 15-801-55) and antibiotics as mentioned under 2 and individual p53 peptides at a final concentration of 80 µg/ml. Subsequently the T2 cells were spun down and treated at a density of $20\times10^6$ cells/ml with Mitomycin C (final concentration 50 µg/ml) in serum-free RPMI 1640 (manufacturer see 2) medium during one hour at 37° C. Thereafter the T2 cells were washed three times in RPMI 1640. Primary CTL responses were induced by filling all wells of a 96-well-U-bottom plate (Costar, Cambridge, Mass., USA, cat. no. 3799) with $1\times10^5$ Mitomycin-C treated T2 cells in 50 µl of medium (serum-free RPMI 1640 containing glutamine and antibiotics as mentioned before), containing peptide at a concentration of 80 µg/ml. To these stimulator cells were added $4\times10^5$ HLA-A2.1 positive PBL in 50 µl of medium to each well. Stimulator and responder cells were cocultured for 7 days at 37° C. in a humidified incubator (90% humidity) and 5% $CO_2$ in air.

5. Cytotoxicity assay

T2 cells were used to target cells, labeled with 100 µCi $^{51}Cr$ for 1 h at 37° C. After labeling the cells were washed twice with serum-free ISCOVE's medium, and then incubated for 60–90 minutes with peptides at 20 µg/ml in a cell concentration of $2\times10^6$ cells per ml in serum-free Iscove's medium. The target cells were washed once more before adding them to the effector cells. Effector target ratio ranged from 20:1 to 2.5:1 in twofold dilution. Cytotoxicity function was tested on 2000 target cells per well in total volume of 100 µl RPMI containing 4% FCS and peptide at a concentration of 20 µg/ml per well. Total duration of the incubation time was 4 h at 37° C.

The percentage $^{51}Cr$ release was calculated by the formula:

$$\frac{\text{cpm experimental well} - \text{background } ^{51}Cr \text{ release}}{\text{cpm 2\% Triton X-100} - \text{background } ^{51}Cr \text{ release}}$$

6. Cloning of CTL by limiting dilution

On days 7 and 14 after primary response induction (see 4) the PBL (responder cells) were restimulated with peptide. To this purpose all cells were harvested. Viable cells were isolated by Ficoll-procedure and washed in RPMI 1640. In a new 96-well-U-bottom plate 50,000 of these viable cells were seeded to each well together with 50 µl medium I (RPMI (Gibco. Paislan, Scotland cat. no. 041-02409)), 15% pooled human serum, glutamine and antibodies as described. Per well 20,000 autologous, irradiated (2500 rad) PBL and 10,000 autologous, irradiated (5000 rad) EBV transformed B lymphocytes were added together with 50 µl of medium II (RPMI (Gibco, Paislan, Scotland cat. no. 041-02409)), 15% pooled human serum, glutamine and antibodies as described and peptide in a final concentration of 80 µg/ml. The cells were cultured for 7 days at 37° C. in an incubator with 5% $CO_2$ and 90% humidity.

On day 21 after primary response initiation, the cultured cells were harvested. Viable cells were isolated by Ficoll-procedure and washed in RPMI 1640. This bulk of viable cells was cloned by limiting dilution. Into each well of a new 96-well-U-bottom plate (Costar, Cambridge, cat. no. 3799) 50 µl medium I was added together with 100, 10, 1 or 0.3 viable cells.

To all the wells 20,000 pooled and irradiated (3000 rad) PBL of at least three different donors and 10,000 pooled and irradiated (10,000 rad) EBV transformed B-cells of at least two different HLA-A2.1 positive donors were added together with 50 µl of medium II, with peptide in a final concentration of 80 µg/ml, LEUCO-AGGLUTININ in a concentration of 2%, human recombinant IL-2 in a concentration of 120 IU/ml (Eurocetus, Amsterdam).

7. Expansion of CTL clones

Individual wells of LD cultures were inspected regularly for cell growth. Cells from wells with expansive growth were transferred to larger culture volumes and repeatedly restimulated with irradiated PBL, HLA-A2.1 positive EBV B cells and p53 peptide as described under 6 and tested for cytotoxicity. Each CTL clone with peptide specific HLA-A2.1 restricted specificity was recloned at least once by the procedure outlined in section 6.

Results

1. Lytic activity of three HLA-A2.1 restricted CTL clones directed against autologous p53 peptide The specific cytotoxic activity of three CTL clones specifically generated against p53 peptide LLGRNSFEV from PBL of a healthy donor by the procedures outlined in section 4, 6 and 7, is shown in Table 3.

TABLE 3

Lytic activity of three p53 peptide specific CTL clones generated following primary peptide driven CTL response initation

| Effectors | E/T | targets T2 + peptide 22 | T2 + peptide 5 | T2 |
|---|---|---|---|---|
| Clone C1 | 20 | 62* | 0 | 0 |
| | 10 | 96 | 0 | 5 |
| | 5 | 79 | 0 | 0 |
| | 2.5 | 70 | 0 | 1 |
| Clone D5 | 20 | 85 | 0 | 12 |
| | 10 | 100 | 0 | 21 |
| | 5 | 89 | 6 | 12 |
| | 2.5 | 100 | 0 | 19 |
| Clone A5 | 20 | 100 | 0 | 5 |
| | 10 | 65 | 0 | 2 |
| | 5 | 76 | 0 | 8 |
| | 2.5 | 74 | 0 | 10 |

*data are expressed as percentage specific $^{51}$Cr release

The CTL Clones C1, A5 and D5 were obtained following an induction of primary CTL responses in vitro with peptide No. 22 loaded T2 cells. The clones were tested for specificity on peptide loaded 51Cr labeled target cells ranging from E/T 20 to E/T 2.5 in twofold dilution steps.

Peptide No. 22 is a peptide of nine amino acids, derived from the wild type p53 protein. Peptide No. 5 is also derived from the wild type p53 sequence and is used as a negative control. Both peptides bind to the HLA-A2.1 molecule, as described in Example 2.

Sequence in one letter codes for the two peptides: No. 22: LLGRNSFEV; NO. 5: RMPEAAPPV. Peptide titration experiments showed that 20 ng/ml of the peptide No. 22 was sufficient for target cell sensitization. The concentration used in this test was 20 μg/ml.

The peptide No. 22-specific clones only lysed HLA-A2.1 positive target cells incubated with p53 peptide No. 22 and not HLA-A2.1 positive target cells not incubated with peptide or incubated with HLA-A2.1 binding p53 peptide No. 5. This result indicates that it is possible to generate a CTL response against an autologous peptide, in this case a peptide of the p53 tumor suppressor gene product, entirely by in vitro induction of response in PBL from a healthy non-immunized HLA-A2.1 positive donor. Similar results so far were obtained in generating p53 specific CTL clones against p53 peptides Nos. 3, 5 and 9.

Reference

1. A. Rogel, M. Popliker, C. G. Webb, M. Oren. p53 cellular tumor antigen: analysis of mRNA levels in normal adult tissues, embryos, and tumors. Mol. Cell. Biol. 5: 2851–2855, 1985.

2. T. Takahashi, M. M. Nau, I. Chiba, M. J. Birrer, R. K. Rosenberg, M. Vinocour, M. Levitt, H. Pass, F. A. Gazdar, J. D. Minna. p53: A frequent target for genetic abnormalities in lung cancer. Science 246: 491–494, 1989.

3. J. M. Nigro, S. J. Baker, A. C. Preisinger, J. M. Jessup, R. Hostetter, K. Cleary, S. H. Bignet, N. Davidson, S. Baylin, P. Devilee, T. Glover, F. S. Collins, A. Weston, R. Modali, C. Harris, B. Vogelstein. Mutations in the p53 gene occur in diverse human rumour types. Nature 342: 705–708, 1989.

4. J. Prosser, A. M. Thompson, G. Cranston, H. J. Evans. Evidence that p53 behaves as a rumour suppressor gene in sporadic breast tumours. Oncogene 5: 1573–1579, 1990.

5. G. Gaidano, P. Ballerini, J. Z. Gong, G. Inghirami, A. Neri, E. W. Newcomb, I. T. Magrath, D. M. Knowles, R. Dallafavera. p53 mutations in human lymphoid malignancies—association with Burkitt lymphoma and chronic lymphocytic leukemia. Proc. Natl. Acad. Sci. USA 88: 5413–5417, 1991.

6. M. R. Stratton, S. Moss, W. Warren, H. Patterson, J. Clark, C. Fisher, C. D. M. Fletcher, A. Ball, M. Thomas, B. A. Gusterson, C. S. Cooper. Mutation of the p53 gene in human soft tissue sarcomas: association with abnormalities of the RB1 gene. Oncogene 5: 1297–1301, 1990.

7. D. Sidransky, A. yon Eschenbach, Y. C. Tsai, P. Jones, I. Summerhayes, F. Marshall, M. Paul, P. Green, S. R. Hamilton, P. Frost, B. Vogelstein. Identification of the p53 gene mutations in bladder cancers and urine samples. Science 252: 706–709, 1991.

8. S. Mashiyama, Y. Murakami, T. Yosimoto, T. Sekiya, K. Hayashi. Detection of p53 gene mutations in human brain tumors by single-strand conformation polymorphism analysis of polymerase chain reactions products. Oncogene 6: 1313–1318, 1991.

9. A. G. Menon, K. M. Anderson, V. M. Riccardi, R. Y. Chung, J. M. Whaley, D. W. Yandell, G. E. Farmer, R. N. Freiman, J. K. Lee, F. P. Li, D. F. Barker, D. H. Ledbetter, A. Kleider, R. L. Martuza, J. F. Gusella, B. R. Seizinger. Chromosome 17p deletions and p53 gene mutations associated with the formation of malignant neurofibrosarcomas in yon Recklinghausen neurofibromatosis. Proc. Natl. Acad. Sci. USA 87: 5435–5439, 1990.

10. T. Soussi, C. C. deFromentel, M. Mechali, P. May, M. Kress. Cloning and characterization of a cDNA from Xenopus laevis coding for a protein homologous to human and murine p53. Oncogene 1: 71–78, 1987.

11. C. A. Finlay, P. W. Hinds, T. H. Tan, D. Eilyahu, M. Oren, A. J. Levine. Activating mutations for transformation by p53 produce a gene product that forms an hsc70-p53 complex with an altered half-life. Mol. Cell. Biol. 8: 531–539, 1988.

12. W. M. Kast and C. J. M. Melief. In vivo efficacy of virus-derived peptides and virus-specific cytotoxic T lymphocytes. Immunology Letters 30:229–232 (1991).

13. C. J. M. Melief. Tumor eradication by adoptive transfer of cytotoxic T lymphocytes. Adv. Cancer Res. 58: 143–175, 1992.

14. G. Reinholdsson-Ljunggren, T. Ramqvist, L. Ährlund-Richter and T. Dalianis. Int. J. Cancer 50:142–146 (1992).

15. R. D. Salter and P. Cresswell. Impaired assembly and transport of HLA-A and -B antigens in a mutant TxB cell hybrid. EMBO J. 5:943–949 (1986).

16. T. Soussi, C. Caron de Fromentel, P. May. Structural aspects of the p53 protein in relation to gene evolution. Oncogene 5: 945–952, 1990.

17. K. Falk, O. Rötzschke, S. Stevanovic, G. Jung, H. G. Rammensee. Allele specific motifs revealed by sequencing of self-peptides eluted from MHC molecules. Nature 351: 290–296, 1991.

18. W. R. Taylor. Identification of Protein Sequence Homology by Consensus Template Alignment. J. Mol. Biol. 188: 233–258 (1986).

19. H. Gausepohl and R. W. Frank. Automatische multiple Peptidsynthese. BioTec (September 1990).

20. H. Gausepohl, M. Kraft, C. Boulin and R. W. Frank. in: E. Giralt and D. Andreu (eds). Peptides 1990, 206–207 (1990).

21. W. Rapp, L. Zhang and E. Bayer. Continuous flow peptide synthesis on PSPOE-Graft-copolymers. In: Innovation and Perspectives in Solid Phase Peptide Synthesis, 205–210 (1990).

22. R. C. Sheppard and B. J. Williams. Acid-labile resin linkage agents for use in solid phase peptide synthesis. Int. J. Peptide Protein Res. 20, 451–454 (1982).

23. H. Gausepohl, M. Kraft and R. Frank. In situ activation of FMOC-amino acids by BOP in solid phase peptide synthesis. Peptides 1988, 241–243 (1988).

24. B. Castro, J. R. Dormoy, G. Erin and C. Selve. Reactifs de couplage peptidique IV (1)-L'hexafluorophosphate de benzotriazolyl N-oxytrisdimethylamino phosphonium (B.O.P.). Tetrahedron Letters 14: 1219–1222 (1975).

25. G. B. Fields and R. L. Noble. Solid phase peptide synthesis utilizing 9-fluorenylmethoxycarbonyl amino acids. Int. J. Peptide Protein Res. 35:161–214 (1990)

26. R. B. Merrifield. Solid phase peptide synthesis. I. The synthesis of a tetra peptide. J. Am. Chem. Soc. 85: 2149–2154 (1963).

27. D. F. Hunt, R. A. Henderson, J. Shabanowitz, K. Sakhuchi, H. Michel, N. Sevilir, A. L. Cox, E. Appella and V. H. Engelhard. Characterization of peptide bound to the Class I MHC molecule HLA-A2.1 by mass spectrometry. Science 255: 1261–1263 (1992).

---

We claim:

1. A peptide consisting of an amino acid sequence derived from human p53 protein,
   wherein said amino acid sequence is selected from the group consisting of SEQ ID NOS: 1–39 and
   wherein said amino acid sequence has the ability to bind to human Major Histocompatibility Complex (MHC) Class I allele HLA-A2.1.

2. A composition containing a peptide consisting of an amino acid sequence derived from human p53 protein, wherein said amino acid sequence is selected from the group consisting of SEQ ID NOS: 1–39 and has the ability to bind to human Major Histocompatibility Complex (MHC) Class I allele HLA-A2.1, and a pharmaceutically acceptable carrier, diluent, excipient or adjuvant.

3. The composition according to claim 2, which is able to induce a cytotoxic T lymphocyte response effective against human p53 protein.

4. The composition according to claim 2, wherein said cytotoxic T lymphocyte response is a HLA Class 1-restricted CD8+ cytotoxic T cell response effective against human p53 protein.

5. A process of inducing a human p53 protein-specific cytotoxic T-lymphocyte response in a T-lymphocyte culture, comprising loading antigen-presenting cells which carry empty Major Histocompatibility Complex (MHC) Class I molecules with a peptide, said peptide consisting of an amine acid sequence derived from human p53 protein, wherein said amine acid sequence is selected from the group consisting of SEQ ID NOS: 1–39 and has the ability to bind to human MHC Class I allele HLA-A2.1, culturing T-lymphocytes in the presence of the peptide-loaded antigen-presenting cells under specific cytotoxic T-lymphocyte response-inducing conditions.

6. The process according to claim 5, further comprising isolating a human p53 protein-specific cytotoxic T lymphocyte and culturing said isolated cytotoxic T-lymphocyte.

7. A human p53 protein-specific cytotoxic T-lymphocyte reactive to a peptide, said peptide consisting of an amino acid sequence derived from human p53 protein, wherein said amine acid sequence is selected from the group consisting of SEQ ID NOS: 1–39 and has the ability to bind to human Major Histocompatibility Complex (MHC) Class I allele HLA-A2.1.

* * * * *

UNITED STATES PATENT AND TRADEMARK OFFICE
CERTIFICATE OF CORRECTION

PATENT NO. : 5,679,641               Page 1 of 3
DATED      : October 21, 1997
INVENTOR(S): Melief et al.

It is certified that error appears in the above-identified patent and that said Letters Patent is hereby corrected as shown below:

| | |
|---|---|
| Column 2, Line 13, | now reads "ELA-A2.1", should read --HLA-A2.1--. |
| Column 2, Line 15, | now reads "Caucasold", should read --Caucasoid--. |
| Column 2, Line 34, | now reads "10-met", should read --10-mer--. |
| Column 2, Line 55, | now reads "10-met", should read --10-mer--. |
| Column 3, Line 36, | now reads "said: amino", should read --said amino--. |
| Column 3, Line 64, | now reads "ALNKMFCOLA", should read --ALNKMFCQLA--. |
| Column 4, Line 9, | now reads "187-193", should read --187-197--. |
| Column 4, Line 28, | now reads "KLFCQLAXT", should read --KLFCQLAKT--. |
| Column 5, Lines 28-29, | now reads "protein-specific specific", should read --protein-specific--. |
| Column 6, Line 22, | now reads "ALNKMFCOLA", should read --ALNKMFCQLA--. |
| Column 6, Line 32, | now reads "187-193", should read --187-197--. |

UNITED STATES PATENT AND TRADEMARK OFFICE
CERTIFICATE OF CORRECTION

PATENT NO.   :   5,679,641
DATED        :   October 21, 1997
INVENTOR(S)  :   Melief et al.

It is certified that error appears in the above-identified patent and that said Letters Patent is hereby corrected as shown below:

| | |
|---|---|
| Column 6, Line 51, | now reads "KLFCQLAXT", should read --KLFCQLAKT--. |
| Column 10, Line 1, | now reads "Tyr, Set", should read --Tyr, Ser--. |
| Column 10, Line 52, | now reads "10.67 M", should read --0.67 M--. |
| Column 11, Line 38, | should contain a section heading --Peptides--. |
| Column 12, Line 2, | now reads "10.9%", should read --0.9%--. |
| Column 13, Line 29, | now reads "Upon routine NIM", should read --upon routine NIH--. |
| Column 13, Line 42, | now reads "(100 Bg/ml,", should read --(100 µg/ml,--. |
| Column 14, Line 14, | now reads "were used to target", should read --were used as target--. |
| Column 15, Line 22, | now reads "96", should read --95--. |
| Column 15, Line 36, | now reads "51Cr", should read --$^{51}$Cr--. |
| Column 16, Line 2, | now reads "S.H. Bignet", should read --S.H. Bigner--. |

UNITED STATES PATENT AND TRADEMARK OFFICE
CERTIFICATE OF CORRECTION

PATENT NO. : 5,679,641
DATED : October 21, 1997
INVENTOR(S) : Melief et al.

It is certified that error appears in the above-identified patent and that said Letters Patent is hereby corrected as shown below:

```
Column 16, line 5, now reads "rumour" should read --tumour--
           line 8, now reads "rumour" should read --tumour--
Column 36, line 15, now reads "amine" should read --amino--
           line 16, now reads "amine" should read --amino--
```

Signed and Sealed this

Fifth Day of May, 1998

Attest:

BRUCE LEHMAN

Attesting Officer

Commissioner of Patents and Trademarks